(12) United States Patent
Yi et al.

(10) Patent No.: US 12,396,753 B2
(45) Date of Patent: Aug. 26, 2025

(54) NEEDLE-TRACT ASSISTANT INCLUDING COMPONENTS AND METHODS THEREOF

(71) Applicant: Becton, Dickinson and Company, Franklin Lakes, NJ (US)

(72) Inventors: Peng Yi, Shanghai (CN); Xiaowen Sun, Shanghai (CN); Zhixiu He, Shanghai (CN); Neville Chia, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 819 days.

(21) Appl. No.: 17/612,189

(22) PCT Filed: May 24, 2019

(86) PCT No.: PCT/CN2019/088318
§ 371 (c)(1),
(2) Date: Nov. 17, 2021

(87) PCT Pub. No.: WO2020/237420
PCT Pub. Date: Dec. 3, 2020

(65) Prior Publication Data
US 2022/0211413 A1     Jul. 7, 2022

(51) Int. Cl.
*A61B 17/34*     (2006.01)
*A61B 17/00*     (2006.01)
(Continued)

(52) U.S. Cl.
CPC ....... *A61B 17/3478* (2013.01); *A61M 25/065* (2013.01); *A61B 2017/00252* (2013.01);
(Continued)

(58) Field of Classification Search
CPC .................. A61B 17/3478; A61M 25/065
See application file for complete search history.

(56) References Cited

U.S. PATENT DOCUMENTS

| 4,808,157 A | 2/1989 | Coombs |
| 4,958,901 A | 9/1990 | Coombs |

(Continued)

FOREIGN PATENT DOCUMENTS

| CN | 107073723 A | 8/2017 |
| CN | 107374702 A | 11/2017 |

(Continued)

OTHER PUBLICATIONS

Bilbao, J., Elorz, M., Vivas, I et al. Transjugular Intrahepatic Portosystemic Shunt (TIPS) in the Treatment of Venous Symptomatic Chronic Portal Thrombosis in Non-cirrhotic Patients. CVIR 27, 474-480 (2004). https://doi.org/10.1007/s00270-004-0241-z (Year: 2004).*

(Continued)

*Primary Examiner* — Erin McGrath
(74) *Attorney, Agent, or Firm* — Rutan & Tucker LLP

(57) ABSTRACT

A needle-tract assistants (100, 200) for establishing a needle tract of a predetermined length, including a needle thruster (110, 210) and a needle-in-catheter assembly (130, 230) removably loaded in the needle thruster (110, 210). The needle thruster (110, 210) can include a cradle (112, 212), a carriage(114, 214) within the cradle (112, 212), and a plunger (116, 216) coupled to the carriages (114, 214). The carriages (114, 214) can be configured to move between a proximal-end portion and a distal-end portion of the cradle (112, 212). The plungers (116, 216) can be configured to move the carriages (114, 214) within the cradle(112, 212). The plungers (116, 216) can also be configured to allow a user to set the predetermined length of the needle tract before establishing the needle tract. The needle-in-catheter assembly (130, 230) can include a hub (132, 232), a catheter tube (134, 234) extending from a distal-end portion of the hub (132, 232), and a needle (137, 237) disposed within the (Continued)

catheter tube (134, 234). Also described are components of the needle-tract assistants (100, 200) and methods of the needle-tract assistants (100, 200) or the components thereof.

23 Claims, 13 Drawing Sheets

(51) Int. Cl.
*A61M 25/00* (2006.01)
*A61M 25/06* (2006.01)
*A61B 90/00* (2016.01)

(52) U.S. Cl.
CPC .................. *A61B 2090/034* (2016.02); *A61M 2025/0095* (2013.01)

(56) References Cited

U.S. PATENT DOCUMENTS

| | | | |
|---|---|---|---|
| 5,360,409 A | 11/1994 | Boyd, III et al. | |
| 5,441,483 A | 8/1995 | Avitall | |
| 5,848,986 A | 12/1998 | Lundquist et al. | |
| 6,117,112 A * | 9/2000 | Mahurkar | A61M 5/322 604/110 |
| 6,171,303 B1 | 1/2001 | Ben-Haim et al. | |
| 8,287,481 B1 | 10/2012 | Kahn et al. | |
| 9,901,675 B2 | 2/2018 | Ella et al. | |
| 2002/0082584 A1 | 6/2002 | Rosenman et al. | |
| 2002/0173751 A1* | 11/2002 | Mastorakis | A61M 5/34 604/218 |
| 2006/0259061 A1 | 11/2006 | Kick et al. | |
| 2007/0191773 A1 | 8/2007 | Wojcik | |
| 2007/0239119 A1 | 10/2007 | Lipov | |
| 2009/0177041 A1 | 7/2009 | Stefanchik et al. | |
| 2011/0137125 A1 | 6/2011 | Belsley | |
| 2011/0152741 A1 | 6/2011 | Banchieri et al. | |
| 2011/0202067 A1 | 8/2011 | Falkner et al. | |
| 2011/0213316 A1 | 9/2011 | Ibrahim et al. | |
| 2012/0221007 A1 | 8/2012 | Batten et al. | |
| 2013/0245533 A1 | 9/2013 | Kahn et al. | |
| 2014/0114330 A1 | 4/2014 | Karasic et al. | |
| 2014/0171826 A1 | 6/2014 | Lampropoulos et al. | |
| 2015/0045769 A1* | 2/2015 | Cabrera Aquino | A61D 7/00 604/117 |
| 2015/0297246 A1 | 10/2015 | Patel et al. | |
| 2016/0106971 A1 | 4/2016 | Servin de la Mora Godinez et al. | |
| 2016/0331443 A1 | 11/2016 | Phan et al. | |
| 2016/0361088 A1 | 12/2016 | Maguire et al. | |
| 2017/0049511 A1 | 2/2017 | Uhm et al. | |
| 2018/0207406 A1 | 7/2018 | Ishida | |
| 2018/0256021 A1 | 9/2018 | Gill | |
| 2018/0256223 A1 | 9/2018 | Lueth et al. | |
| 2018/0344985 A1 | 12/2018 | Shah et al. | |
| 2019/0117937 A1 | 4/2019 | Humphrey et al. | |
| 2019/0184136 A1 | 6/2019 | Lubinski et al. | |
| 2019/0282217 A1 | 9/2019 | Graham et al. | |
| 2019/0282218 A1 | 9/2019 | Panzenbeck et al. | |
| 2022/0240981 A1 | 8/2022 | Yi et al. | |
| 2022/0241562 A1 | 8/2022 | Yi et al. | |
| 2024/0225692 A1 | 7/2024 | Forreiter | |

FOREIGN PATENT DOCUMENTS

| | | |
|---|---|---|
| CN | 107412935 A | 12/2017 |
| CN | 107661552 A | 2/2018 |
| CN | 108618739 A | 10/2018 |
| WO | 9724983 A2 | 7/1997 |
| WO | 98/56293 A1 | 12/1998 |
| WO | 2008/014791 A1 | 2/2008 |
| WO | 2008121888 A1 | 10/2008 |
| WO | 2010115134 A1 | 10/2010 |
| WO | 14071161 A1 | 5/2014 |
| WO | 14100349 A1 | 6/2014 |
| WO | 2018/022432 A1 | 2/2018 |
| WO | 2020237420 A1 | 12/2020 |
| WO | 2022242874 A1 | 11/2022 |

OTHER PUBLICATIONS

PCT/CN2019/088318 filed May 24, 2019 International Search Report and Written Opinion dated Feb. 6, 2020.
EP 19930992.3 filed Nov. 24, 2021 Extended European Search Report dated Oct. 18, 2022.
EP 199310871 filed Nov. 24, 2021 Extended European Search Report dated Nov. 3, 2022.
PCT/CN2019/088334 filed May 24, 2019 International Search Report and Written Opinion dated Feb. 6, 2020.
PCT/CN2019/088347 filed May 24, 2019 International Search Report and Written Opinion dated Feb. 12, 2020.
PCT/EP2021/063619 filed May 21, 2021 International Search Report and Written Opinion dated Feb. 14, 2022.
U.S. Appl. No. 17/612,188, filed Nov. 17, 2021 Final Office Action dated Oct. 1, 2024.
U.S. Appl. No. 17/612,188, filed Nov. 17, 2021 Non-Final Office Action dated Jun. 20, 2024.
U.S. Appl. No. 17/612,188, filed Nov. 17, 2021 Non-Final Office Action dated Nov. 25, 2024.
U.S. Appl. No. 17/612,196, filed Nov. 17, 2021 Non-Final Office Action dated Nov. 19, 2024.

\* cited by examiner

NEEDLE-TRACT ASSISTANT INCLUDING COMPONENTS AND METHODS THEREOF

PRIORITY

This application is a U.S. national stage application of International Application No. PCT/CN2019/088318, filed May 24, 2019, which is incorporated by reference in its entirety into this application.

BACKGROUND

In a healthy person, blood flowing from the stomach, esophagus, or intestines first flows through the liver. In an unhealthy person having, for example, liver damage, there can be blood flow-restricting blockages in the liver such that blood cannot easily flow therethrough. Such a condition is known as portal hypertension. Common causes of portal hypertension include alcohol abuse, too much iron in the liver (e.g., hemochromatosis), hepatitis B, hepatitis C, or blood clots in a vein that flows from the liver to the heart. When portal hypertension occurs, the blood flow-restricting blockages can elevate pressure in the portal vein causing it to rupture and seriously bleed. A person with portal hypertension can also have bleeding from the veins of the stomach, esophagus, or intestines (e.g., variceal bleeding), a buildup of fluid in the belly (e.g., ascites), or a buildup of fluid in the chest (e.g., hydrothorax).

Portal hypertension is often treated by way of a percutaneous procedure involving placement of a transjugular intrahepatic portosystemic shunt ("TIPS") between the hepatic vein and the portal vein as shown in FIG. 13 to establish blood flow through the liver. Placement of a portosystemic shunt between the right hepatic vein and the right portal vein is generally preferred. A typical procedure for placing a portosystemic shunt in accordance with the foregoing includes placing an introducer sheath in a distal portion of the right hepatic vein followed by advancing a stiffening cannula, optionally as part of a cannula-in-catheter assembly, through the introducer sheath to the distal portion of the right hepatic vein. A needle-in-catheter assembly is subsequently inserted into the stiffening cannula, the stiffening cannula is wedged against the wall of the right hepatic vein, and the needle-in-catheter assembly is thrust through the liver parenchyma into the right portal vein with a single needle throw. However, such a needle throw is blindly performed. As such, there is a risk of overshooting the portal vein in such procedures, which can introduce complications, prolong the procedures, decrease success rates, and the like.

Disclosed herein is a needle-tract assistant including components and methods thereof that address at least the forgoing shortcomings.

SUMMARY

Disclosed herein is a needle-tract assistant for establishing a needle tract of a predetermined length. The needle-tract assistant includes, in some embodiments, a needle thruster and a needle-in-catheter assembly removably loaded in the needle thruster. The needle thruster includes a cradle, a carriage within the cradle, and a plunger coupled to the carriage. The carriage is configured to move between a proximal-end portion and a distal-end portion of the cradle. The plunger is configured to move the carriage within the cradle. The plunger is also configured to allow a user to set the predetermined length of the needle tract before establishing the needle tract. The needle-in-catheter assembly includes a hub, a catheter tube extending from a distal-end portion of the hub, and a needle disposed within the catheter tube.

In some embodiments, the cradle of the needle thruster includes a longitudinal opening between the proximal-end portion and the distal-end portion of the cradle. The longitudinal opening is configured to allow the needle-in-catheter assembly to be removed from the needle thruster through the opening.

In some embodiments, the cradle of the needle thruster includes a proximal-end opening at a proximal end of the cradle and a distal-end opening at a distal end of the cradle. The plunger extends through the proximal-end opening of the cradle. The catheter tube and needle extend through the distal-end opening of the cradle when the needle-in-catheter assembly is disposed in the needle thruster.

In some embodiments, the cradle of the needle thruster includes a longitudinal rail extending along an inner surface of the cradle. The longitudinal rail is configured to guide movement of the plunger, the carriage, or both the plunger and the carriage within the cradle.

In some embodiments, the plunger of the needle thruster includes a longitudinal channel extending along an outer surface of the plunger. The longitudinal channel is configured to receive the longitudinal rail of the cradle.

In some embodiments, the cradle of the needle thruster includes a spiral rail spiraling around an inner surface of the cradle. The spiral rail is configured to guide movement of the plunger, the carriage, or both the plunger and the carriage within the cradle. The spiral rail is also configured to govern a linear velocity of the plunger, the carriage, or both the plunger and the carriage within the cradle.

In some embodiments, the cradle of the needle thruster includes a spiral channel spiraling around an outer surface of the plunger. The spiral channel is configured to receive the spiral rail of the cradle.

In some embodiments, the carriage of the needle thruster includes an unloading mechanism for unloading the needle-in-catheter assembly from the carriage.

In some embodiments, the unloading mechanism includes a compression spring-loaded lever shaped to form a proximal-end portion of a receptacle in the carriage. The receptacle is configured to receive the hub of the needle-in-catheter assembly. The lever is configured to compress the spring of the unloading mechanism upon pressing the lever toward the cradle. By pressing the lever toward the cradle, lever assumes a spring force of the unloading-mechanism spring and increases a length of the receptacle, which allows the hub of the needle-in-catheter assembly to be removed from the receptacle.

In some embodiments, the hub of the needle-in-catheter assembly includes a loading mechanism for loading the needle-in-catheter assembly in the carriage.

In some embodiments, the loading mechanism includes a compression spring-loaded proximal-end cap of the hub of the needle-in-catheter assembly. The proximal-end cap is configured to move toward the distal-end portion of the hub and compress the spring of the loading mechanism upon loading the hub in the receptacle of the carriage. A spring force exerted by the loading-mechanism spring holds the hub in the receptacle of the carriage.

In some embodiments, the hub of the needle-in-catheter assembly includes an internal chamber in a proximal-end portion of the hub. A port of the hub and one or more microlumens longitudinally extending through the catheter tube are fluidly connected to the internal chamber.

In some embodiments, the needle of the needle-in-catheter assembly extends through the internal chamber of the hub without a fluid connection with the internal chamber of the hub.

In some embodiments, a distal end of the needle of the needle-in-catheter assembly distally extends beyond a distal end of the catheter tube of the of the needle-in-catheter assembly. A distal-end portion of the catheter tube including the distal end of the catheter tube has a tapered distal tip including one or more openings corresponding to the one or more microlumens of the catheter tube.

Also disclosed herein is a needle-in-catheter assembly for establishing a needle tract. The needle-in-catheter assembly includes a hub, a catheter tube extending from a distal-end portion of the hub, and a needle disposed within the catheter tube. The catheter tube is a double-walled catheter tube including an outer wall and an inner wall. The needle is fixed to a compression spring-loaded proximal-end cap of the hub.

In some embodiments, the needle is disposed within a needle lumen longitudinally extending through the catheter tube. The needle lumen is defined by an inner surface of the inner wall of the catheter tube.

In some embodiments, the catheter tube includes one or more microlumens longitudinally extending through the catheter tube. Each of the one or more microlumens defined by an inner surface of the outer wall of the catheter tube, an outer surface of the inner wall of the catheter tube, and one or more struts longitudinally extending through the catheter tube between the outer wall and the inner wall of the catheter tube.

In some embodiments, the hub includes an internal chamber in a proximal-end portion of the hub. A port of the hub and the one or more microlumens are fluidly connected to the internal chamber.

In some embodiments, the needle extends through the internal chamber of the hub without a fluid connection with the internal chamber.

In some embodiments, a distal end of the needle distally extends beyond a distal end of the catheter tube. A distal-end portion of the catheter tube including the distal end of the catheter tube has a tapered distal tip including one or more openings corresponding to the one or more microlumens of the catheter tube.

In some embodiments, the hub includes a loading mechanism including the proximal-end cap of the hub for loading the needle-in-catheter assembly in a carriage of a needle thruster. The proximal-end cap is configured to move toward the distal-end portion of the hub and compress the spring of the loading mechanism upon loading the hub in a receptacle of the carriage. A spring force exerted by the loading-mechanism spring holds the hub in the receptacle of the carriage.

In some embodiments, the hub includes a longitudinal handle extending from the hub between a proximal-end portion and the distal-end portion of the hub.

Also disclosed herein is a method of establishing a needle tract of a predetermined length with a needle-tract assistant. The method includes, in some embodiments, inserting a needle-in-catheter assembly into a stiffening cannula disposed in an introducer sheath positioned in a hepatic vein, the needle-in-catheter assembly including a needle having a distal end extending beyond that of a catheter surrounding the needle; moving a plunger of a needle thruster to set a carriage coupled to the plunger in position within a cradle of the needle thruster for establishing the needle tract of the predetermined length; loading a hub of the needle-in-catheter assembly in the carriage of the needle thruster; and thrusting the plunger of the needle thruster toward a distal end of the needle thruster to thrust the needle-in-catheter assembly through a liver parenchyma into a portal vein, thereby forming the needle tract of the predetermined length.

In some embodiments, the method further includes radiographically determining a length for the needle tract of the predetermined length before setting the carriage of the needle thruster in position within the cradle for establishing the needle tract of the predetermined length.

In some embodiments, the method further includes radiographically confirming a length of the needle tract after forming the needle tract of the predetermined length by counting a number of evenly spaced radiopaque rings on the catheter of the needle-in-catheter assembly.

These and other features of the concepts provided herein will become more apparent to those of skill in the art in view of the accompanying drawings and following description, which disclose particular embodiments of such concepts in greater detail.

DRAWINGS

DESCRIPTION

Figure 1:
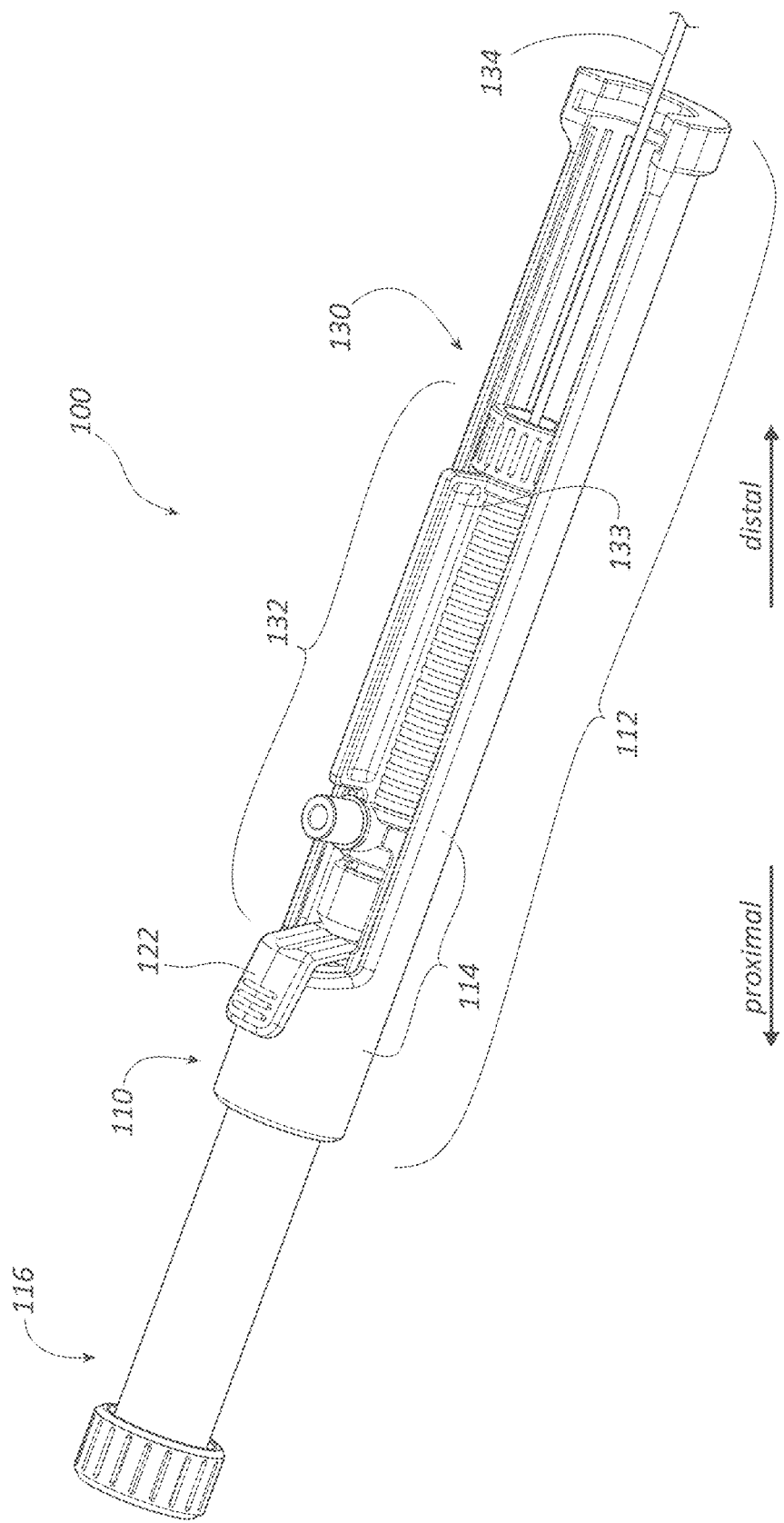
FIG. 1 illustrates a first view of a first needle-tract assistant, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Figure 13:
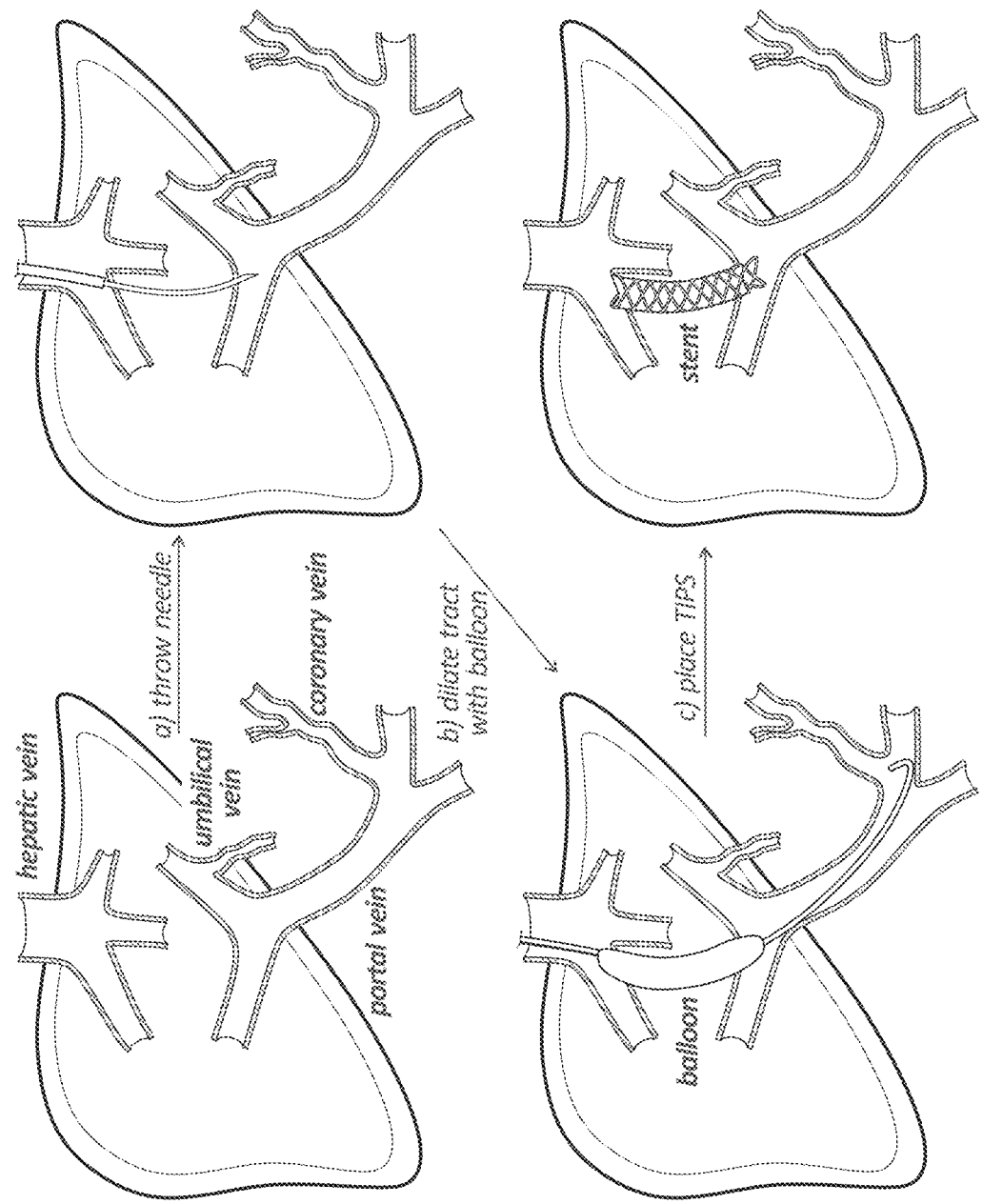
FIG. 13 illustrates a procedure involving placement of a TIPS between a hepatic vein and a portal vein, in accordance with some embodiments.

As set forth above, portal hypertension is often treated by way of a percutaneous procedure involving placement of a TIPS between the hepatic vein and the portal vein as shown in FIG. 13 to establish blood flow through the liver. Placement of a portosystemic shunt between the right hepatic vein and the right portal vein is generally preferred. A typical procedure for placing a portosystemic shunt in accordance with the foregoing includes placing an introducer sheath in a distal portion of the right hepatic vein followed by advancing a stiffening cannula, optionally as part of a cannula-in-catheter assembly, through the introducer sheath to the distal portion of the right hepatic vein. A needle-in-catheter assembly is subsequently inserted into the stiffening cannula, the stiffening cannula is wedged against the wall of the right hepatic vein, and the needle-in-catheter assembly is thrust through the liver parenchyma into the right portal vein with a single needle throw. However, such a needle throw is blindly performed. As such, there is a risk of overshooting the portal vein in such procedures, which can introduce complications, prolong the procedures, decrease success rates, and the like.

Disclosed herein is a needle-tract assistant including components and methods thereof that address at least the forgoing shortcomings.

Figure 2:
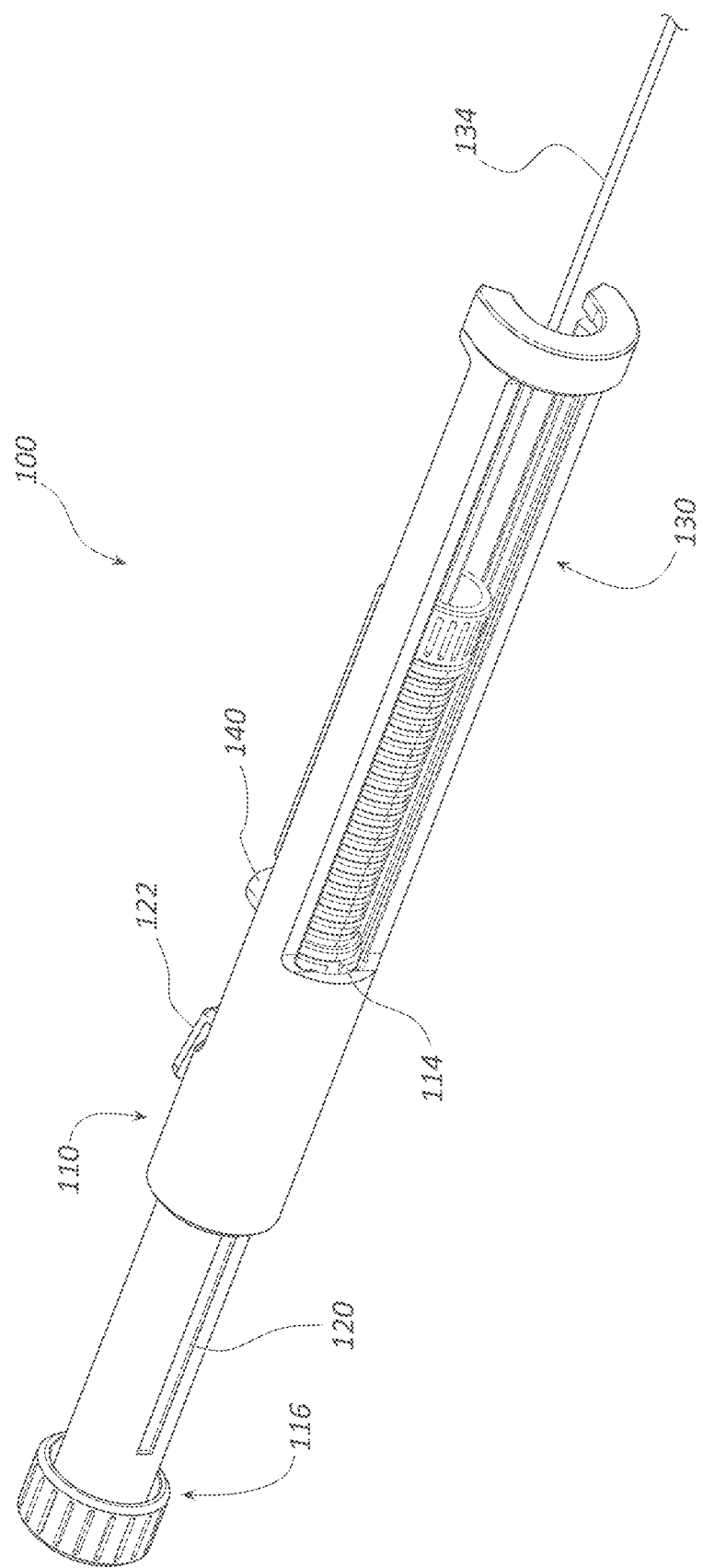
FIG. 2 illustrates a second view of the first needle-tract assistant, in accordance with some embodiments.
Figure 3:
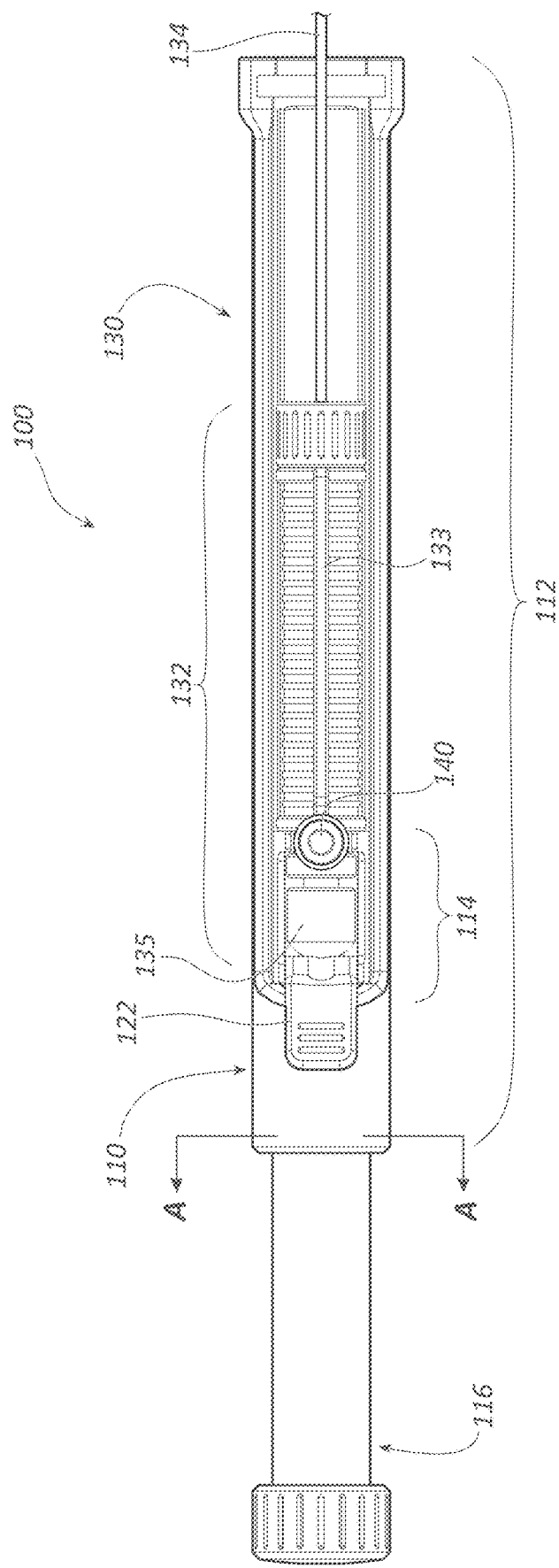
FIG. 3 illustrates a third view of the first needle-tract assistant, in accordance with some embodiments.
Figure 4:
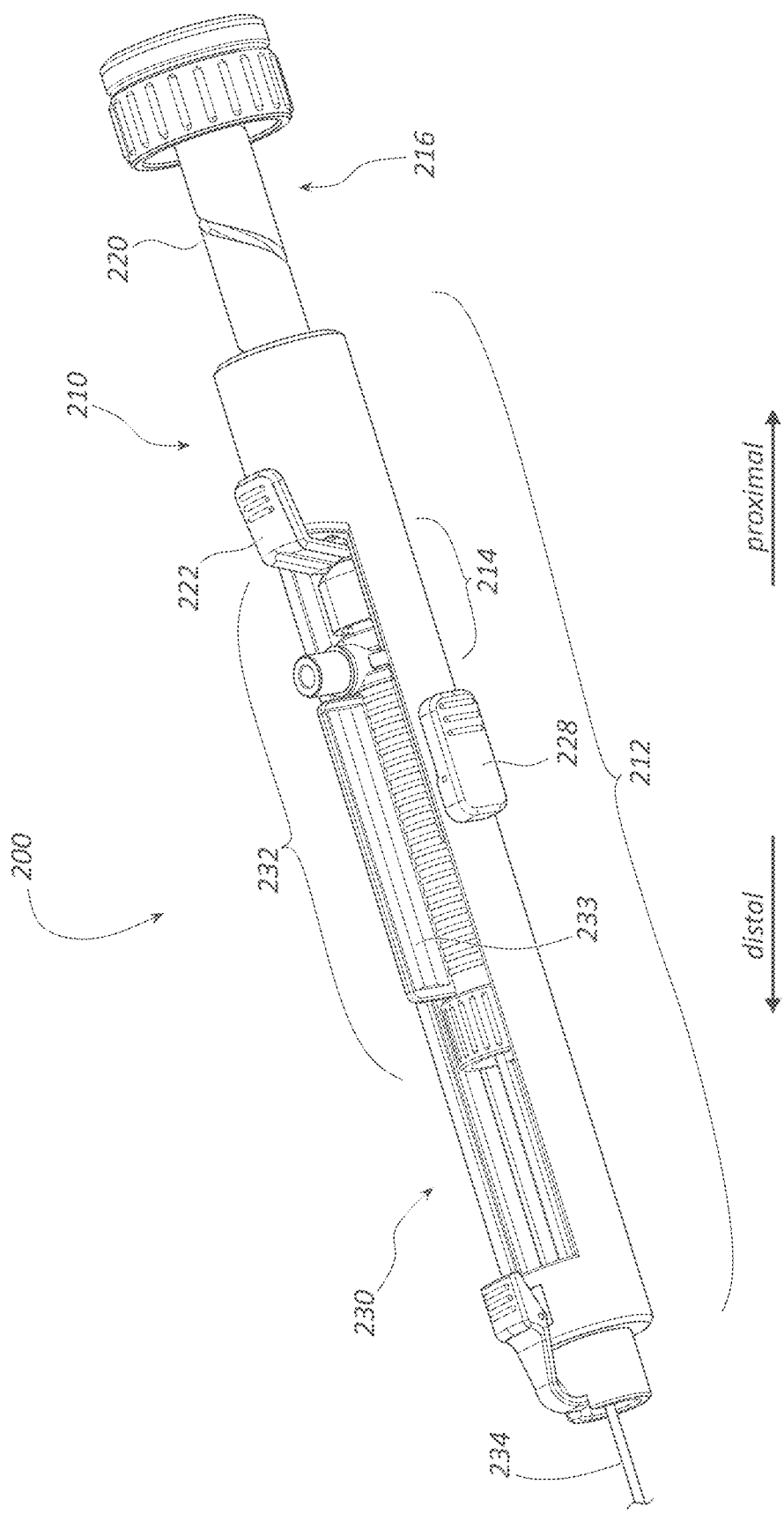
FIG. 4 illustrates a first view of a second needle-tract assistant, in accordance with some embodiments.
Figure 5:
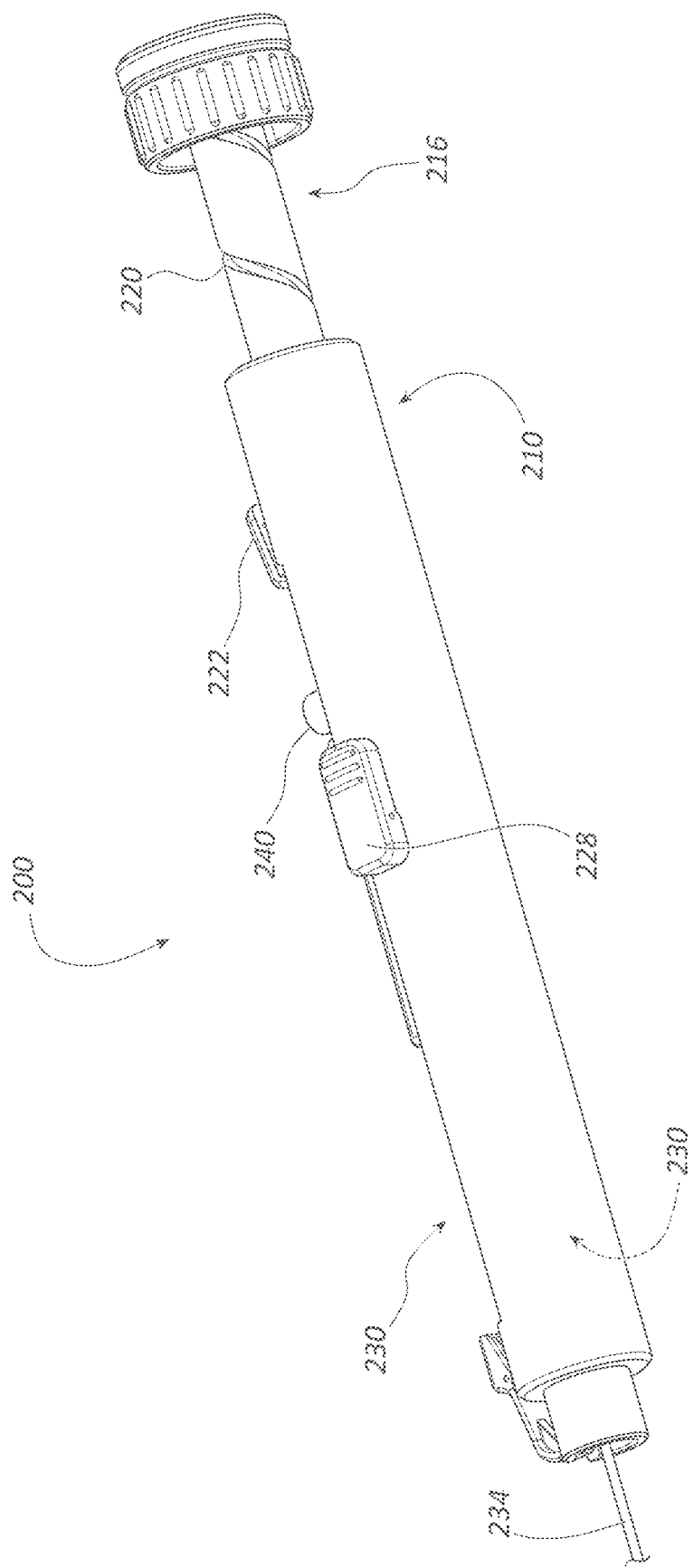
FIG. 5 illustrates a second view of the second needle-tract assistant, in accordance with some embodiments.
Figure 6:
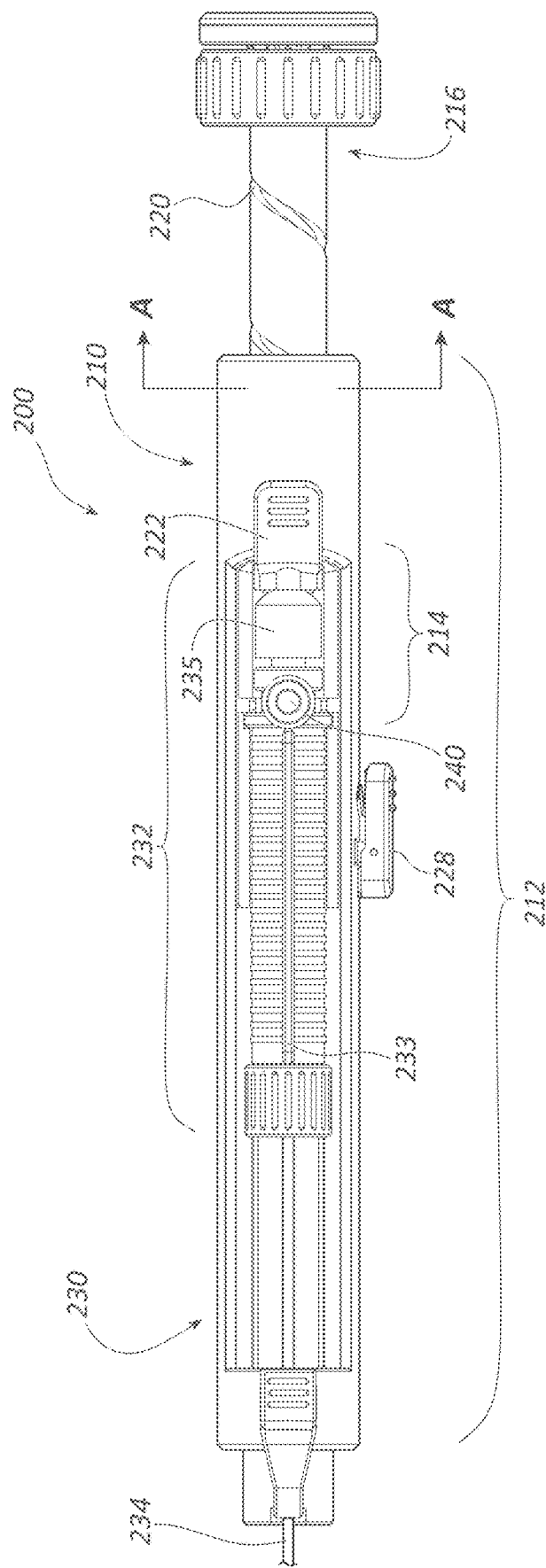
FIG. 6 illustrates a third view of the second needle-tract assistant, in accordance with some embodiments.
Figure 7:
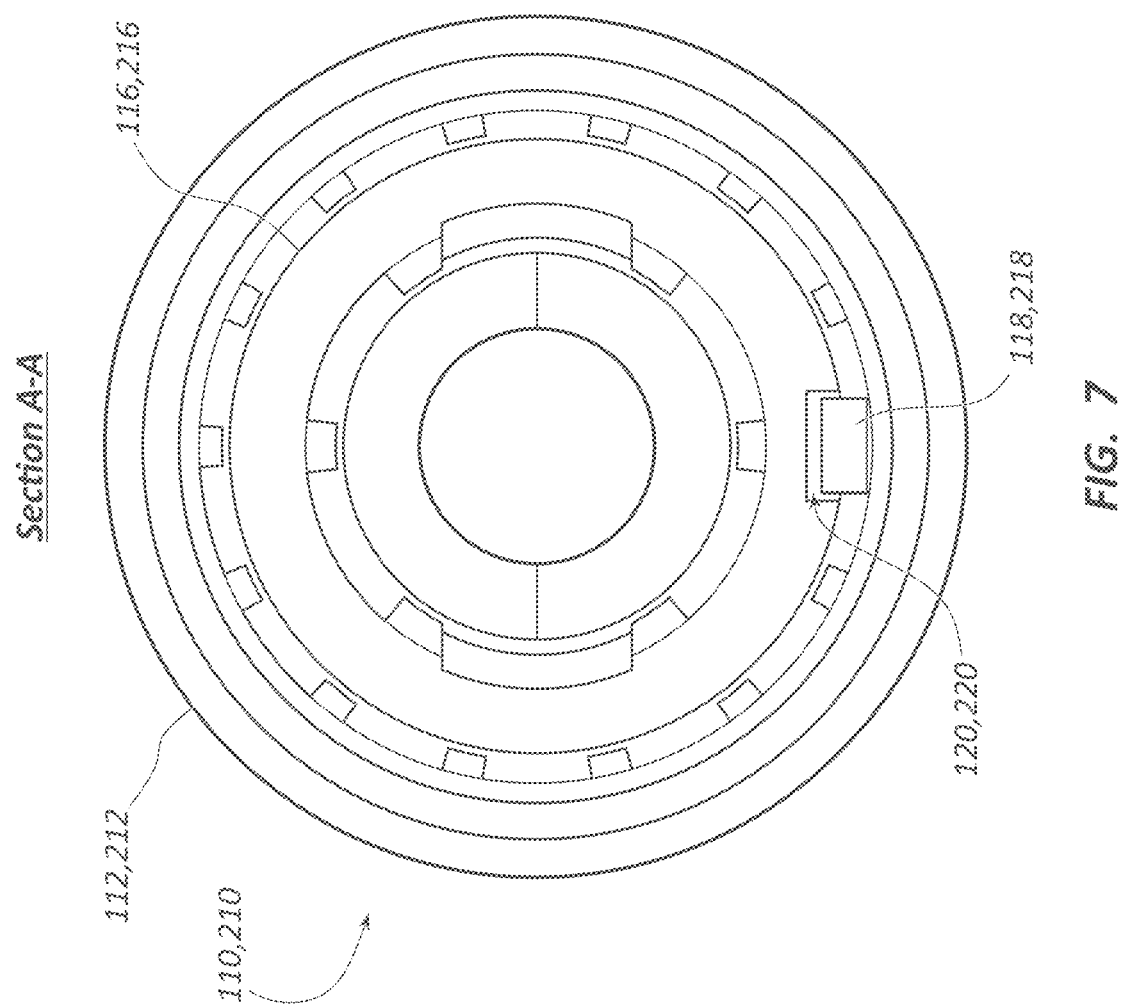
FIG. 7 illustrates a transverse cross section of either the first needle-track assistant or the second needle-tract assistant, in accordance with some embodiments.
Figure 10:
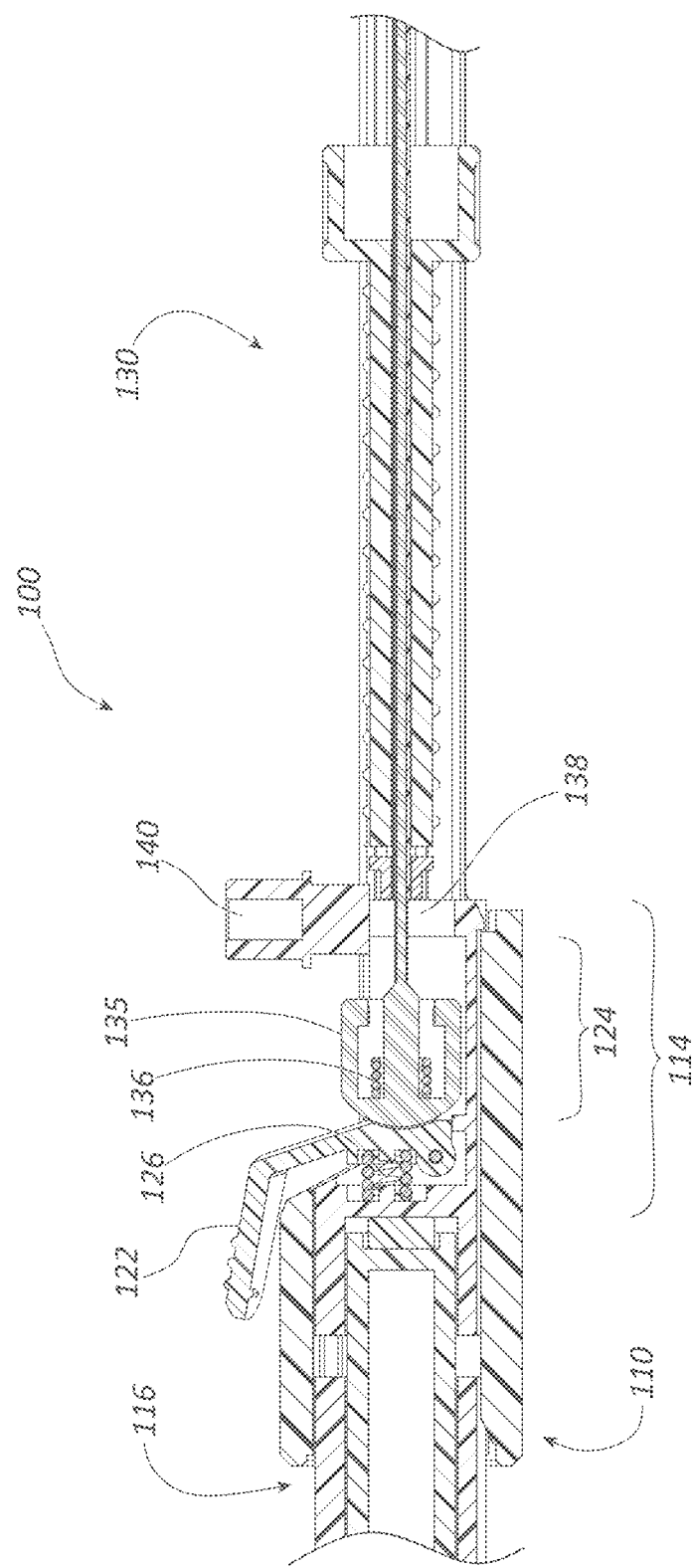
FIG. 10 illustrates a first view of a longitudinal cross section of the first needle-tract assistant, in accordance with some embodiments.
Figure 11:
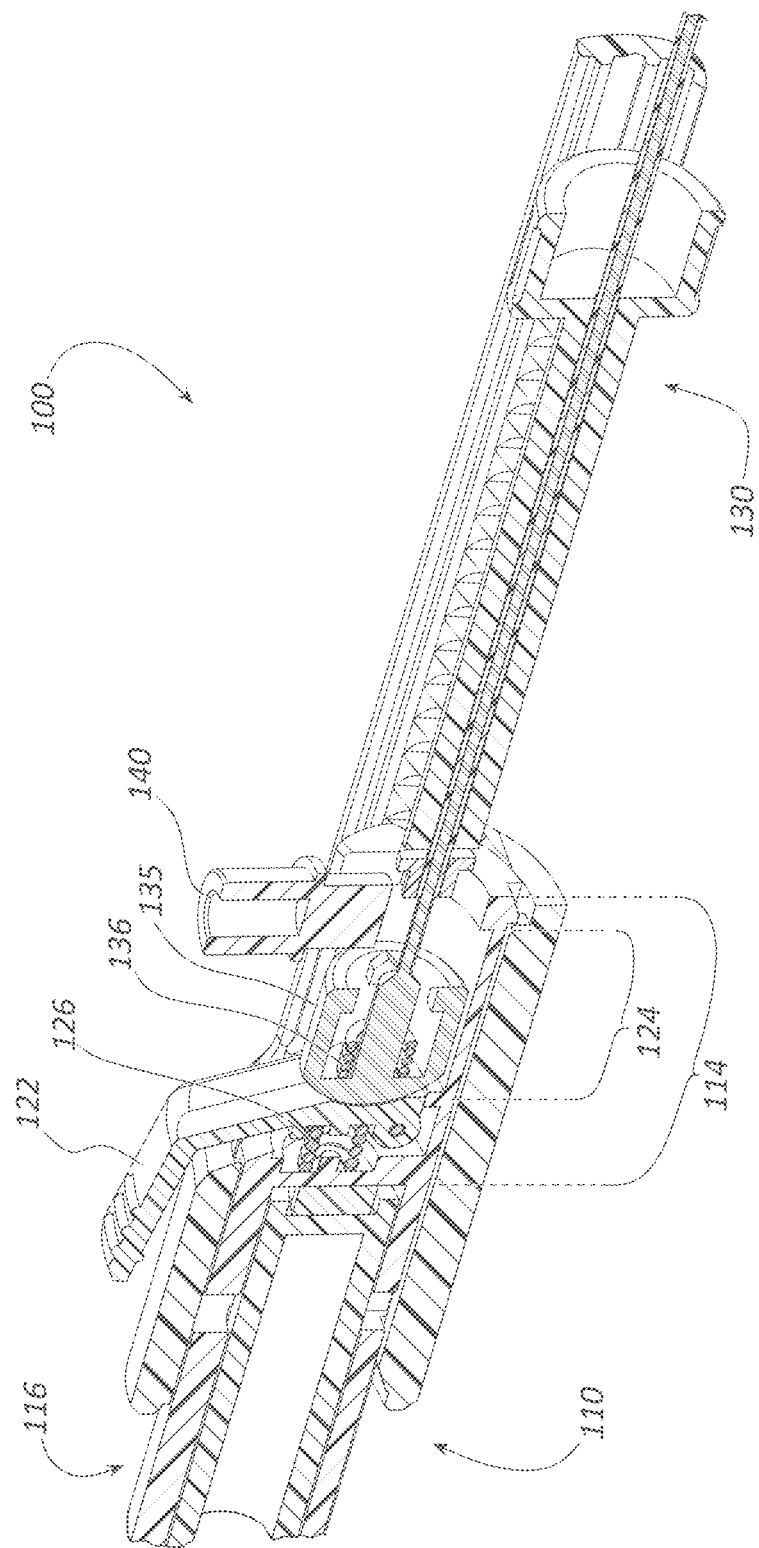
FIG. 11 illustrates a second view of a longitudinal cross section of the first needle-tract assistant, in accordance with some embodiments.
Figure 12:
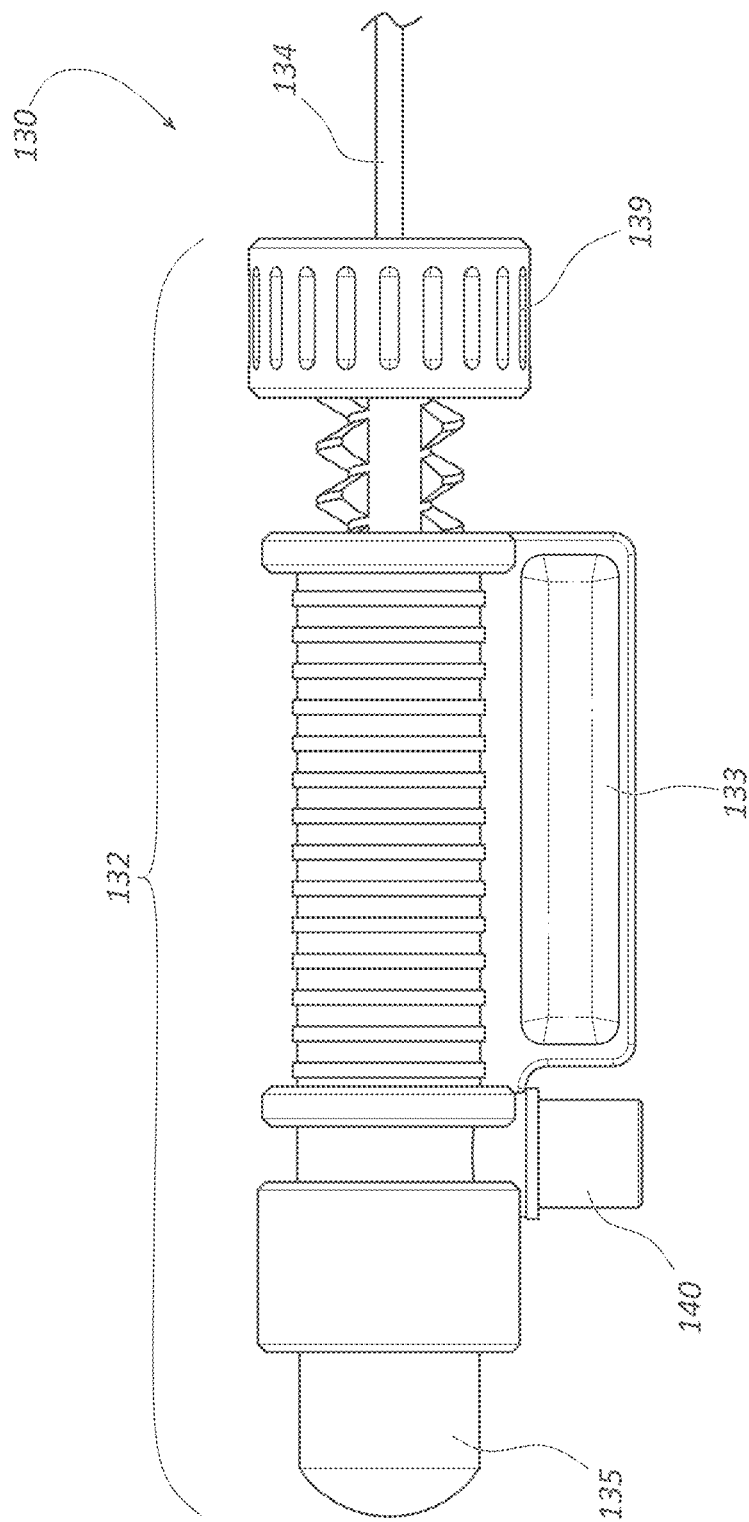
FIG. 12 illustrates a catheter tube-advancing mechanism of a hub of a needle-in-catheter assembly, in accordance with some embodiments.

FIGS. 1-3 illustrate different views of a first needle-tract assistant 100, in accordance with some embodiments. FIGS. 4-6 illustrate different views of a second needle-tract assistant 200, in accordance with some embodiments. FIG. 7 illustrates a transverse cross section of either the first needle-track assistant 100 or the second needle-tract assistant 200, in accordance with some embodiments. FIGS. 10 and 11 illustrate different views of a longitudinal cross section of the first needle-tract assistant 100, in accordance with some embodiments. FIG. 12 illustrates a catheter tube-advancing mechanism of a hub 132 of a needle-in-catheter assembly 130 or 230, in accordance with some embodiments.

The needle-tract assistant 100 or 200 includes a needle thruster 110 or 210 and the needle-in-catheter assembly 130 or 230 removably loaded in the needle thruster 110 or 210.

Beginning with the needle thruster 110 or 210, the needle thruster 110 includes a cradle 112 or 212, a carriage 114 or 214 movably disposed within the cradle 112 or 212, and a plunger 116 or 216 coupled to the carriage 114 or 214. Each of the cradle 112 or 212, the carriage 114 or 214, and the plunger 116 or 216 will now be described.

The cradle 112 or 212 of the needle thruster 110 or 210 includes a longitudinal opening between a proximal-end portion and a distal-end portion of the cradle 112 or 212. The longitudinal opening is configured to allow the needle-in-catheter assembly 130 or 230 to be inserted or removed from the needle thruster 110 or 210 through the opening.

The cradle 112 or 212 of the needle thruster 110 or 210 includes a proximal-end opening at a proximal end of the cradle 112 or 212 and a distal-end opening at a distal end of the cradle 112 or 212. The plunger 116 or 216 extends through the proximal-end opening of the cradle 112 or 212. A catheter tube 134 or 234 and a needle 137 or 237 extend through the distal-end opening of the cradle 112 or 212 when the needle-in-catheter assembly 130 or 230 is disposed in the needle thruster 110 or 210. While configured differently for each needle thruster of the needle thrusters 110 and 210, the distal-end opening at the distal end of the cradle 112 or 212 has smaller dimensions (e.g., diameter, width, etc.) than a distal end of the needle-in-catheter assembly 130 or 230, thereby providing a stop for the needle-in-catheter assembly 130 or 230.

The cradle 112 of the needle thruster 110 includes a longitudinal rail 118 extending along an inner surface of the cradle 112. The longitudinal rail 118 is configured to guide movement of the plunger 116, the carriage 114, or both the plunger 116 and the carriage 114 within the cradle 112. Differently, the cradle 212 of the needle thruster 210 includes a spiral rail 218 spiraling around an inner surface of the cradle 212. The spiral rail 218 is configured to guide movement of the plunger 216, the carriage 214, or both the plunger 216 and the carriage 214 within the cradle 212. The spiral rail 218 is also configured to govern a linear velocity of the plunger 216, the carriage 214, or both the plunger 216 and the carriage 214 within the cradle 212.

The carriage 114 or 214 of the needle thruster 110 or 210 is configured to move between the proximal-end portion and the distal-end portion of the cradle 112 or 212 such as on a same or different rail than the longitudinal rail 118 or spiral rail 218 along the inner surface of the cradle 112 or 212.

The carriage 114 or 214 of the needle thruster 110 or 210 includes an unloading mechanism for unloading the needle-in-catheter assembly 130 or 230 from the carriage 114 or 214. The unloading mechanism includes a compression spring-loaded lever 122 or 222 shaped to form a proximal-end portion of a receptacle 124 or 224 (not shown) in the carriage 114 or 214. (For the receptacle 224, see the receptacle 124 of FIGS. 10 and 11. The receptacle 224 is analogous to the receptacle 124.) The receptacle 124 or 224 is configured to receive the hub 132 or 232 of the needle-in-catheter assembly 130 or 230. The lever 122 or 222 is configured to compress the spring 126 or 226 (not shown) of the unloading mechanism upon pressing the lever 122 or 222 toward the cradle 112 or 212. (For the spring 226, see the spring 126 of FIGS. 10 and 11. The spring 226 is analogous to the spring 126.) By pressing the lever 122 or 222 toward the cradle 112 or 212, the lever 122 or 222 assumes a spring force of the unloading-mechanism spring 126 or 226 and increases a length of the receptacle 124 or 224, which allows the hub 132 or 232 of the needle-in-catheter assembly 130 or 230 to be removed from the receptacle 124 or 224.

The plunger 116 or 216 of the needle thruster 110 or 210 is configured to move the carriage 114 or 214 within the cradle 112 or 212. The plunger 116 of the needle thruster 110 includes a longitudinal channel 120 extending along an outer surface of the plunger 116. The longitudinal channel 120 is configured to receive the longitudinal rail 118 of the cradle 112. Differently, the plunger 216 of the needle thruster 210 includes a spiral channel 220 spiraling around an outer surface of the plunger 216. The spiral channel 220 is configured to receive the spiral rail 218 of the cradle 212.

The plunger 116 or 216 of the needle thruster 110 or 210 is also configured to allow a user to set the carriage 114 or 214 within the cradle 112 or 212 in accordance with the predetermined length of the needle tract before establishing the needle tract. The needle thruster 210 is different from the needle thruster 110 in that the needle thruster 210 is also configured to allow the user to lock the carriage 214 within the cradle 212 once set in accordance with the predetermined length of the needle tract before establishing the needle tract. As best shown in FIG. 6, the needle thruster 210 includes a compression spring-loaded lever 228 along a longitudinal side of the cradle 212. The lever 228 includes a tooth configured to extend through the longitudinal side of the cradle 212 and engage a toothed rack incorporated into the carriage 214 when the spring between the lever 228 and the longitudinal side of the cradle 212 is in its most relaxed state, thereby locking the carriage 214 within the cradle 212. When the lever 228 is pressed toward the longitudinal side of the cradle 212, the tooth disengages the toothed rack of the carriage 214 so the plunger can freely move the carriage 214 to set the carriage 214 in accordance with the predetermined length of the needle tract before establishing the needle tract.

With the exception of the compression spring 126 or 226, which can be made of, for example, stainless steel, the needle thruster 110 or 210 can be made by molding pieces of the needle thruster 110 or 210 and coupling the resulting molded pieces together to make the needle thruster 110 or 210. The molded pieces can be molded by, for example, injection molding with polyethylene, polycarbonate, or some other medically acceptable thermoplastic. The molded pieces can be coupled together by pressing the molded pieces together if configured with snap-together connectors, adhering the molded pieces together with an adhesive, bonding the molded pieces together with solvent, or a combination thereof.

Adverting to the needle-in-catheter assembly 130 or 230, the needle-in-catheter assembly 130 or 230 includes the hub 132 or 232, the catheter tube 134 or 234 extending from a distal-end portion of the hub 132 or 232, and the needle 137 or 237 disposed within the catheter tube 134 or 234. (See FIG. 8.) Each of the hub 132 or 232, the catheter tube 134 or 234, and the needle 137 or 237 will now be described.

The hub 132 or 232 of the needle-in-catheter assembly 130 or 230 includes a longitudinal handle 133 or 233 extending from the hub 132 or 232 between a proximal-end portion and the distal-end portion of the hub 132 or 232. The handle 133 or 233 is configured for handling the needle-in-catheter assembly 130 or 230. For example, the handle 133 or 233 can be used to manipulate the needle-in-catheter assembly 130 or 230 when using the needle-in-catheter assembly 130 or 230 separately from the needle thruster 110 or 210, loading the needle-in-catheter assembly 130 or 230 in the needle thruster 110 or 210, or when unloading the needle-in-catheter assembly 130 or 230 from the needle thruster 110 or 210.

The hub 132 or 232 of the needle-in-catheter assembly 130 or 230 includes a catheter tube-advancing mechanism for advancing the catheter tube 134 or 234 with respect to the needle 137 or 237. The catheter tube-advancing mechanism includes a threaded distal-end plug 139 or 239 (not shown) of the hub 132 or 232 of the needle-in-catheter assembly 130 or 230. (For the distal-end plug 239, see the distal-end plug 139 of FIG. 12. The distal-end plug 239 is analogous to the distal-end plug 139.) The distal-end plug 139 or 239 of the catheter tube-advancing mechanism is configured to advance from the distal-end portion of the hub 132 or 232 upon turning the distal-end plug 139 or 239 in a first direction. Upon turning the distal-end plug 139 or 239 in a second direction, the catheter tube-advancing mechanism is configured to withdraw the distal-end plug 139 or 239 into the distal-end portion of the hub 132 or 232. Because the catheter tube 134 or 234 is fixedly attached to the distal-end plug 139 or 239, the catheter tube 134 or 234 is also advanced from the distal-end portion of the hub 132 or 232 upon turning the distal-end plug 139 or 239 in the first direction and withdrawn into the distal-end portion of the hub 132 or 232 upon turning the distal-end plug 139 or 239 in the second direction. The catheter tube-advancing mechanism allows the catheter tube 134 or 234 to be advanced up to or beyond a distal tip of the needle 137 or 237 such as after establishing the needle tract of the predetermined length with the needle-in-catheter assembly 130 or 230. The needle 137 or 237 can be subsequently removed from the needle-in-catheter assembly 130 or 230 by disconnecting a compression spring-loaded proximal-end cap 135 or 235 of the hub 132 or 232 of the needle-in-catheter assembly 130 or 230 and withdrawing the needle 137 or 237 from the needle-in-catheter assembly 130 or 230.

The hub 132 or 232 of the needle-in-catheter assembly 130 or 230 includes a loading mechanism for loading the needle-in-catheter assembly 130 or 230 in the carriage 114 or 214. The loading mechanism includes the compression spring-loaded proximal-end cap 135 or 235 of the hub 132 or 232 of the needle-in-catheter assembly 130 or 230. The proximal-end cap 135 or 235 is configured to move toward the distal-end portion of the hub 132 or 232 and compress the spring 136 or 236 (not shown) of the loading mechanism upon loading the hub 132 or 232 in the receptacle 124 or 224 of the carriage 114 or 214. (For the spring 236, see the spring 136 of FIGS. 10 and 11. The spring 236 is analogous to the spring 136.) A spring force exerted by the loading-mechanism spring 136 or 236 holds the hub 132 or 232 in the receptacle 124 or 224 of the carriage 114 or 214.

The hub 132 or 232 of the needle-in-catheter assembly 130 or 230 optionally includes a needle-advancing mechanism for advancing the needle 137 or 237 with respect to the catheter tube 134 or 234 or both the needle 137 or 237 and the catheter tube 134 or 234 together with respect the hub 132 or 232. Such a needle-advancing mechanism can include a threaded needle-advancing mechanism configured to advance the needle 137 or 237 or both the needle and the catheter tube 134 or 234 together upon turning a threaded element (e.g., the proximal-end cap 135 or 235) of the threaded needle-advancing mechanism in a first direction. Upon turning the threaded element in a second direction, the threaded needle-advancing mechanism is configured to retract the needle 137 or 237 or both the needle and the catheter tube 134 or 234 together. Such a needle-advancing mechanism can alternatively include a slide-based needle-advancing mechanism configured to advance the needle 137 or 237 or both the needle and the catheter tube 134 or 234 together upon sliding a slideable element (e.g., a tab disposed in a longitudinal slot of the handle 133 or 233) of the slideable needle-advancing mechanism in a first direction. Upon sliding the slideable element in a second direction, the slideable needle-advancing mechanism is configured to retract the needle 137 or 237 or both the needle and the catheter tube 134 or 234 together.

The hub 132 or 232 of the needle-in-catheter assembly 130 or 230 includes an internal chamber 138 or 238 (not shown) in a proximal-end portion of the hub 132 or 232. (For the internal chamber 238, see the internal chamber 138 of FIGS. 10 and 11. The internal chamber 238 is analogous to the internal chamber 138.) A port 140 or 240 of the hub 132 or 232 and one or more microlumens 141 or 241 longitudinally extending through the catheter tube 134 or 234 are fluidly connected to the internal chamber 138 or 238. The needle 137 or 237 of the needle-in-catheter assembly 130 or 230 extends through the internal chamber 138 or 238 of the hub 132 or 232 without a fluid connection with the internal chamber 138 or 238 of the hub 132 or 232. The needle 137 or 237 is fixed to the proximal-end cap 135 or 235 of the hub 132 or 232.

Figure 8:
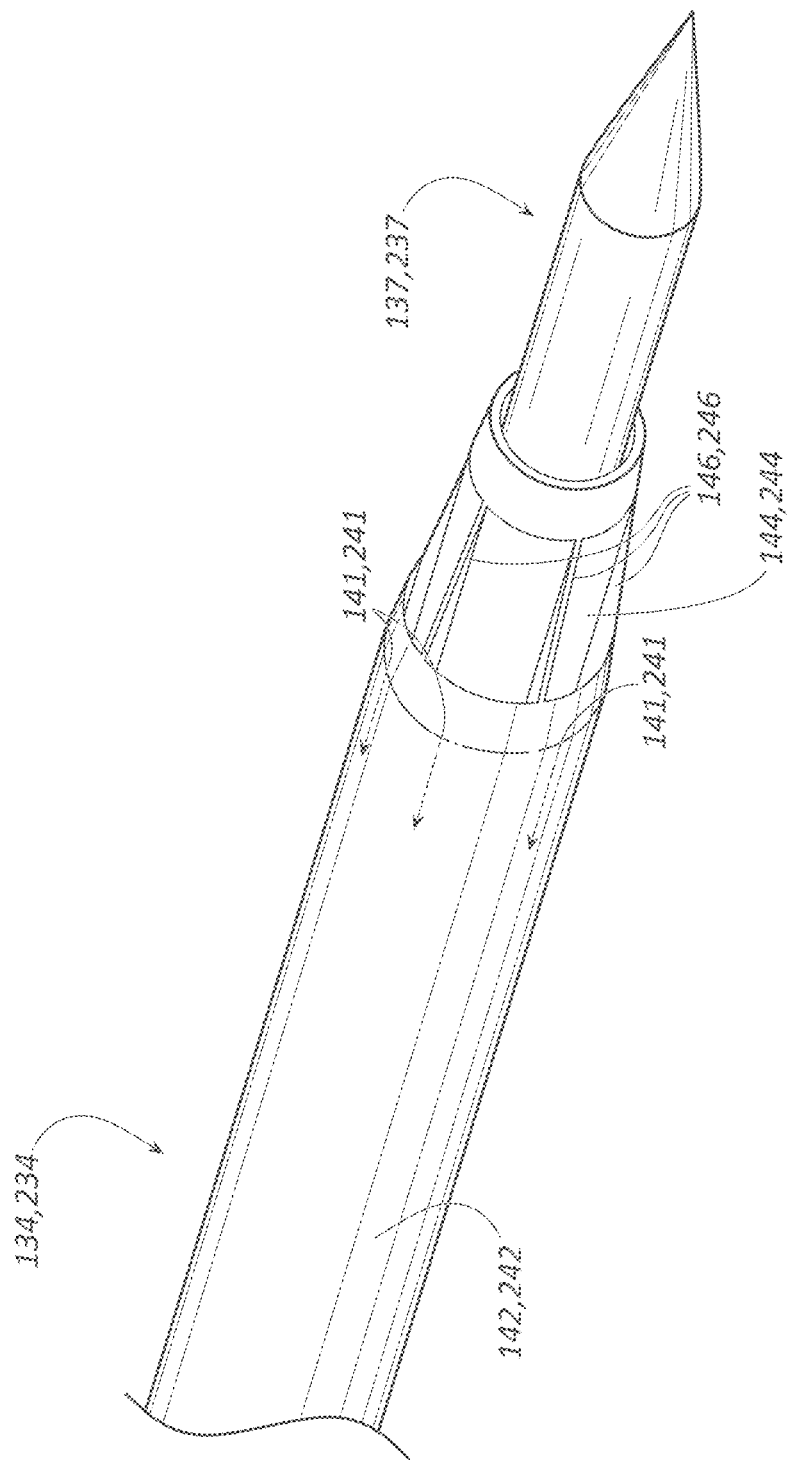
FIG. 8 illustrates a first view of a distal-end portion of a needle disposed in a catheter tube, in accordance with some embodiments.
Figure 9:
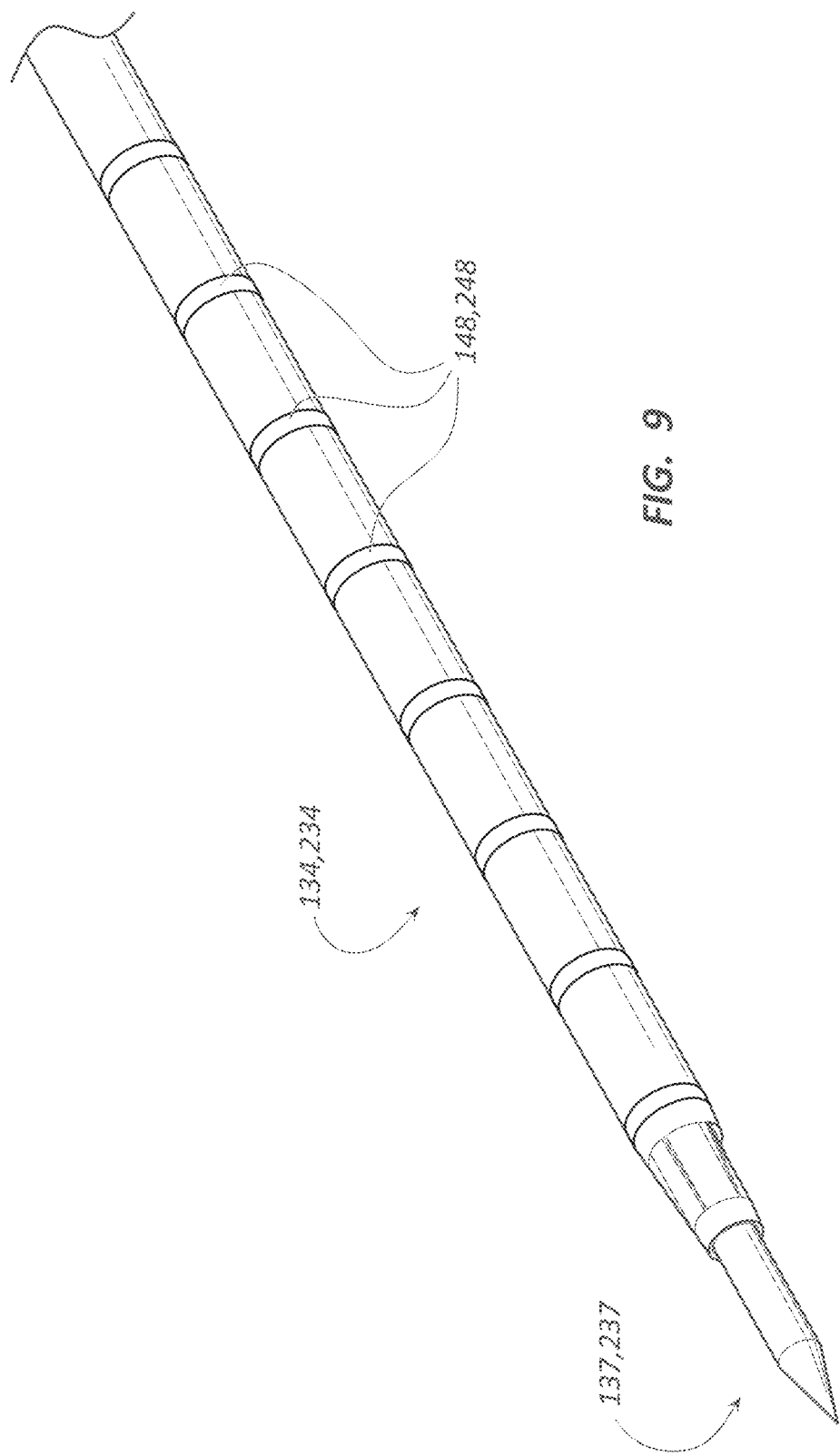
FIG. 9 illustrates a second of a distal-end portion of a needle disposed in a catheter tube, in accordance with some embodiments.

FIGS. 8 and 9 illustrate different views of a distal-end portion of the needle 137 or 237 disposed in the catheter tube 134 or 234, in accordance with some embodiments.

The catheter tube 134 or 234 of the needle-in-catheter assembly 130 or 230 is a double-walled catheter tube including an outer wall 142 or 242 and an inner wall 144 or 244. A distal-end portion of the catheter tube 134 or 234 including a distal end of the catheter tube 134 or 234 has a tapered distal tip including one or more openings corresponding to one or more microlumens 141 or 241 of the catheter tube 134 or 234. Each of the one or more microlumens 141 or 241 is defined by an inner surface of the outer wall 142 or 242 of the catheter tube 134 or 234, an outer surface of the inner wall 144 or 244 of the catheter tube 134 or 234, and one or more struts 146 or 246 longitudinally extending through the catheter tube 134 or 234 between the outer wall 142 or 242 and the inner wall 144 or 244 of the catheter tube 134 or 234. The one or more microlumens 141 or 241 are configured to allow a bodily fluid such as blood to flash back into the internal chamber 138 or 238 for drawing the bodily fluid from the port 140 or 240 without withdrawing the needle 137 or 237.

The catheter tube 134 or 234 of the needle-in-catheter assembly 130 or 230 can include a number of evenly spaced radiopaque rings 148 or 248 on the catheter tube 134 or 234 for radiographically confirming a length of the needle tract after forming the needle tract of the predetermined length by counting of the needle-in-catheter assembly 130 or 230.

The needle 137 or 237 of the needle-in-catheter assembly 130 or 230 can be a hollow needle or a solid needle as shown. A distal end of the needle 137 or 237 distally extends beyond the distal end of the catheter tube 134 or 234 of the of the needle-in-catheter assembly 130 or 230. The needle 137 or 237 is disposed within a needle lumen longitudinally extending through the catheter tube 134 or 234. The needle lumen is defined by an inner surface of the inner wall 144 or 244 of the catheter tube 134 or 234.

With the exception of the cannula tube 134 or 234, the needle 137 or 237, and the compression spring 136 or 236, which can respectively be made of polyurethane, stainless steel, and stainless steel, the needle-in-catheter assembly 130 or 230 such as the hub 132 or 232 can be made by molding pieces of the needle-in-catheter assembly 130 or 230 and coupling the resulting molded pieces together to make the needle-in-catheter assembly 130 or 230. The molded pieces can be molded by, for example, injection molding with polyethylene, polycarbonate, or some other medically acceptable thermoplastic. The molded pieces can be coupled together by pressing the molded pieces together if configured with snap-together connectors, adhering the molded pieces together with an adhesive, bonding the molded pieces together with solvent, or a combination thereof.

Methods

Each needle-tract assistant of the needle-tract assistants 100 and 200 is configured for establishing a needle tract of a predetermined length during at least a procedure involving placing a portosystemic shunt between the hepatic vein and the portal vein, which reduces the risk of overshooting the portal vein. As such, the needle-tract assistants 100 and 200 can reduce complications, shorten procedure times, increase success rates, and the like for procedures such as the foregoing procedure.

A method of establishing a needle tract of a predetermined length with the needle-tract assistant 100 or 200 includes inserting the needle-in-catheter assembly 130 or 230 into a stiffening cannula disposed in an introducer sheath positioned in a hepatic vein, the needle-in-catheter 130 or 230 assembly including the needle 137 or 237 having the distal end extending beyond that of the catheter tube 134 or 234 surrounding the needle 137 or 237; moving the plunger 116 or 216 of the needle thruster 110 or 210 to set the carriage 114 or 214 coupled to the plunger 116 or 216 in position within the cradle 112 or 212 of the needle thruster 110 or 210 for establishing the needle tract of the predetermined length; loading the hub 132 or 232 of the needle-in-catheter assembly 130 or 230 in the carriage 114 or 214 of the needle thruster 110 or 210; and thrusting the plunger 116 or 216 of the needle thruster 110 or 210 toward a distal end of the needle thruster 110 or 210 to thrust the needle 137 or 237 and catheter tube 134 or 234 of the needle-in-catheter assembly 130 or 230 through a liver parenchyma into a portal vein, thereby forming the needle tract of the predetermined length.

The method further includes advancing the catheter tube 134 or 234 up to or beyond the distal tip of the needle 137 or 237 after establishing the needle tract of the predetermined length by turning the distal-end plug 139 or 239 in the first direction; and removing the needle 137 or 237 from the needle-in-catheter assembly 130 or 230 by disconnecting the proximal-end cap 135 or 235 of the hub 132 or 232 of the needle-in-catheter assembly 130 or 230 and withdrawing the needle 137 or 237 from the needle-in-catheter assembly 130 or 230.

The method further includes radiographically determining a length for the needle tract of the predetermined length before setting the carriage 114 or 214 of the needle thruster 110 or 210 in position within the cradle 114 or 214 for establishing the needle tract of the predetermined length.

The method further includes radiographically confirming the length of the needle tract after forming the needle tract of the predetermined length by counting a number of the evenly spaced radiopaque rings 148 or 248 on the catheter tube 134 or 234 of the needle-in-catheter assembly 130 or 230.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A needle-tract assistant for establishing a needle tract of a predetermined length, comprising:
   a needle thruster including:
      a cradle;
      a carriage within the cradle, the carriage configured to move between a proximal-end portion and a distal-end portion of the cradle; and
      a plunger coupled to the carriage, the plunger configured to move the carriage within the cradle and allow a user to set the predetermined length of the needle tract before establishing the needle tract; and
   a needle-in-catheter assembly including:
      a hub;
      a catheter tube extending from a distal-end portion of the hub; and
      a needle disposed within the catheter tube, the needle-in-catheter assembly removably loaded in the carriage of the needle thruster, wherein:
         a distal end of the needle extends distally beyond a distal end of the catheter tube, and
         the distal-end portion of the catheter tube includes a tapered distal tip including one or more openings corresponding to one or more microlumens of the catheter tube.

2. The needle-tract assistant of claim 1, wherein the cradle of the needle thruster includes a longitudinal opening between the proximal-end portion and the distal-end portion of the cradle configured to allow the needle-in-catheter assembly to be removed from the needle thruster through the longitudinal opening.

3. The needle-tract assistant of claim 1, wherein the cradle of the needle thruster includes a proximal-end opening at a proximal end of the cradle through which the plunger extends and a distal-end opening at a distal end of the cradle through which the catheter tube and the needle extend when the needle-in-catheter assembly is disposed in the needle thruster.

4. The needle-tract assistant of claim 1, wherein the cradle of the needle thruster includes a longitudinal rail extending along an inner surface of the cradle configured to guide movement of the plunger, the carriage, or both the plunger and the carriage within the cradle.

5. The needle-tract assistant of claim 4, wherein the plunger of the needle thruster includes a longitudinal channel extending along an outer surface of the plunger configured to receive the longitudinal rail of the cradle.

6. The needle-tract assistant of claim 1, wherein the cradle of the needle thruster includes a spiral rail spiraling around an inner surface of the cradle configured to guide movement of the plunger, the carriage, or both the plunger and the carriage within the cradle and govern a linear velocity thereof.

7. The needle-tract assistant of claim 6, wherein the plunger of the needle thruster includes a spiral channel spiraling around an outer surface of the plunger configured to receive the spiral rail of the cradle.

8. The needle-tract assistant of claim 1, wherein the carriage of the needle thruster includes a first component configured to unload the needle-in-catheter assembly from the carriage.

9. The needle-tract assistant of claim 8, wherein the first component includes a compression spring-loaded lever shaped to form a proximal-end portion of a receptacle in the carriage configured to receive the hub of the needle-in-catheter assembly, the compression spring-loaded lever configured to compress a spring of the first component upon pressing the compression spring-loaded lever toward the cradle, thereby assuming a spring force of an unloading-mechanism spring, increasing a length of the receptacle, and allowing the hub of the needle-in-catheter assembly to be removed from the receptacle.

10. The needle-tract assistant of claim 9, wherein the hub of the needle-in-catheter assembly includes a second component configured to load the needle-in-catheter assembly in the carriage.

11. The needle-tract assistant of claim 10, wherein the second component includes a compression spring-loaded proximal-end cap of the hub of the needle-in-catheter assembly, the compression spring-loaded proximal-end cap configured to move toward the distal-end portion of the hub and compress a spring of the second component upon loading the hub in the receptacle of the carriage, thereby allowing a spring force exerted by the spring of the second component to hold the hub in the receptacle of the carriage.

12. The needle-tract assistant of claim 1, wherein the hub of the needle-in-catheter assembly includes an internal chamber in a proximal-end portion of the hub to which a port of the hub and one or more microlumens longitudinally extending through the catheter tube are fluidly connected.

13. The needle-tract assistant of claim 12, wherein the needle of the needle-in-catheter assembly extends through the internal chamber of the hub without a fluid connection with the internal chamber.

14. A needle-in-catheter assembly for establishing a needle tract, comprising:
   a hub;
   a double-walled catheter tube extending from a distal-end portion of the hub, the double-walled catheter tube including an outer wall, an inner wall, and one or more microlumens longitudinally extending through the double-walled catheter tube, each of the one or more microlumens defined by an inner surface of the outer wall of the double-walled catheter tube, an outer surface of the inner wall of the double-walled catheter tube, and one or more struts longitudinally extending through the double-walled catheter tube between the outer wall and the inner wall of the double-walled catheter tube; and a needle disposed within the double-walled catheter tube, the needle fixed to a compression spring-loaded proximal-end cap of the hub.

15. The needle-in-catheter assembly of claim 14, wherein the needle is disposed within a needle lumen longitudinally extending through the double-walled catheter tube, the needle lumen defined by an inner surface of the inner wall of the double-walled catheter tube.

16. The needle-in-catheter assembly of claim 14, wherein the hub includes an internal chamber in a proximal-end portion of the hub to which a port of the hub and the one or more microlumens are fluidly connected.

17. The needle-in-catheter assembly of claim 16, wherein the needle extends through the internal chamber of the hub without a fluid connection with the internal chamber.

18. The needle-in-catheter assembly of claim 14, wherein a distal end of the needle distally extends beyond a distal end of the double-walled catheter tube, a distal-end portion of the double-walled catheter tube including the distal end of the double-walled catheter tube having a tapered distal tip including one or more openings corresponding to the one or more microlumens of the double-walled catheter tube.

19. The needle-in-catheter assembly of claim 14, wherein the compression spring-loaded proximal-end cap of the hub is configured to move toward the distal-end portion of the hub and compress a spring upon loading the hub in a receptacle of a carriage, thereby allowing a spring force exerted by the spring to hold the hub in the receptacle of the carriage.

20. The needle-in-catheter assembly of claim 14, wherein the hub includes a longitudinal handle extending from the hub between a proximal-end portion and the distal-end portion of the hub.

21. A needle-tract assistant for establishing a needle tract of a predetermined length, comprising:
    a needle thruster including:
        a cradle;
        a carriage within the cradle, the carriage configured to move between a proximal-end portion and a distal-end portion of the cradle, the carriage including a first component configured to unload a needle-in-catheter assembly from the carriage; and
        a plunger coupled to the carriage, the plunger configured to move the carriage within the cradle and allow a user to set the predetermined length of the needle tract before establishing the needle tract; and
    the needle-in-catheter assembly including:
        a hub including a second component configured to load the needle-in-catheter assembly in the carriage;
        a catheter tube extending from a distal-end portion of the hub; and
        a needle disposed within the catheter tube, the needle-in-catheter assembly removably loaded in the carriage of the needle thruster, wherein:
            the first component includes a compression spring-loaded lever shaped to form a proximal-end portion of a receptacle in the carriage configured to receive the hub, and
            the compression spring-loaded lever is configured to compress a spring of the first component upon pressing the compression spring-loaded lever toward the cradle, thereby assuming a spring force of an unloading-mechanism spring, increasing a length of the receptacle, and allowing the hub of the needle-in-catheter assembly to be removed from the receptacle.

22. A needle-tract assistant for establishing a needle tract of a predetermined length, comprising:
    a needle thruster including:
        a cradle;
        a carriage within the cradle, the carriage configured to move between a proximal-end portion and a distal-end portion of the cradle; and
        a plunger coupled to the carriage, the plunger configured to move the carriage within the cradle and allow a user to set the predetermined length of the needle tract before establishing the needle tract; and
    a needle-in-catheter assembly including:
        a hub including an internal chamber in a proximal-end portion of the hub;
        a catheter tube extending from a distal-end portion of the hub, wherein a port of the hub and one or more microlumens longitudinally extending through the catheter tube are fluidly connected to the internal chamber; and
        a needle disposed within the catheter tube, the needle-in-catheter assembly removably loaded in the carriage of the needle thruster.

23. The needle-tract assistant of claim 22, wherein the needle of the needle-in-catheter assembly extends through the internal chamber of the hub without a fluid connection with the internal chamber.

* * * * *